(12) United States Patent
Boyce et al.

(10) Patent No.: US 8,364,224 B2
(45) Date of Patent: Jan. 29, 2013

(54) SYSTEM AND METHOD FOR FACILITATING SENSOR AND MONITOR COMMUNICATION

(75) Inventors: Robin Boyce, Pleasanton, CA (US); Brad Nordstrom, Alameda, CA (US); Arie Ravid, Rishon-Lezion (IL); Hui Wang, San Ramon, CA (US)

(73) Assignee: Covidien LP, Mansfield, MA (US)

( * ) Notice: Subject to any disclaimer, the term of this patent is extended or adjusted under 35 U.S.C. 154(b) by 973 days.

(21) Appl. No.: 12/415,244

(22) Filed: Mar. 31, 2009

(65) Prior Publication Data

US 2009/0247852 A1    Oct. 1, 2009

Related U.S. Application Data

(60) Provisional application No. 61/072,598, filed on Mar. 31, 2008.

(51) Int. Cl.
*A61B 5/1455* (2006.01)
*G06F 19/00* (2011.01)

(52) U.S. Cl. ........................................ 600/331; 600/323

(58) Field of Classification Search .................. 600/331, 600/332, 323
See application file for complete search history.

(56) References Cited

U.S. PATENT DOCUMENTS

| | | |
|---|---|---|
| 3,638,640 A | 2/1972 | Shaw |
| 4,714,341 A | 12/1987 | Hamaguri et al. |
| 4,796,636 A | 1/1989 | Branstetter et al. |
| 4,805,623 A | 2/1989 | Jöbsis |
| 4,807,631 A | 2/1989 | Hersh et al. |
| 4,911,167 A | 3/1990 | Corenman et al. |
| 4,913,150 A | 4/1990 | Cheung et al. |
| 4,936,679 A | 6/1990 | Mersch |
| 4,938,218 A | 7/1990 | Goodman et al. |
| 4,971,062 A | 11/1990 | Hasebe et al. |
| 4,972,331 A | 11/1990 | Chance |
| 4,974,591 A | 12/1990 | Awazu et al. |
| 5,028,787 A | 7/1991 | Rosenthal et al. |
| 5,065,749 A | 11/1991 | Hasebe et al. |
| 5,084,327 A | 1/1992 | Stengel |
| 5,119,815 A | 6/1992 | Chance |
| 5,122,974 A | 6/1992 | Chance |

(Continued)

FOREIGN PATENT DOCUMENTS

| | | |
|---|---|---|
| DE | 69123448 | 5/1997 |
| EP | 1491135 | 12/2004 |

(Continued)

OTHER PUBLICATIONS

Barreto, Armando B., et al.; "Adaptive LMS Delay Measurement in dual Blood Volume Pulse Signals for Non-Invasive Monitoring," IEEE, pp. 117-120 (1997).

(Continued)

*Primary Examiner* — Sean P Dougherty
*Assistant Examiner* — Michael C Stout
(74) *Attorney, Agent, or Firm* — Fletcher Yoder

(57) ABSTRACT

Embodiments disclosed herein may include an adapter which is capable of converting signals from an oximeter sensor such that the signals are readable by an oximeter monitor. In an embodiment, the adapter is capable of converting signals relating to calibration information from the oximeter sensor. The calibration information may relate to wavelengths of light emitting diodes within the oximeter sensor. In a specific embodiment, the adapter will convert wavelength calibration information in a first form relating to data values stored in a digital memory chip to a second form relating to a resistance value of an expected resistor within the oximeter sensor.

18 Claims, 5 Drawing Sheets

U.S. PATENT DOCUMENTS

| | | | |
|---|---|---|---|
| 5,167,230 A | 12/1992 | Chance | |
| 5,190,038 A | 3/1993 | Polson et al. | |
| 5,246,003 A | 9/1993 | DeLonzor | |
| 5,247,931 A | 9/1993 | Norwood | |
| 5,249,576 A | 10/1993 | Goldberger et al. | |
| 5,259,381 A | 11/1993 | Cheung et al. | |
| 5,263,244 A | 11/1993 | Centa et al. | |
| 5,275,159 A | 1/1994 | Griebel | |
| 5,279,295 A | 1/1994 | Martens et al. | |
| 5,287,853 A | 2/1994 | Vester et al. | |
| 5,297,548 A | 3/1994 | Pologe | |
| 5,355,880 A | 10/1994 | Thomas et al. | |
| 5,372,136 A | 12/1994 | Steuer et al. | |
| 5,385,143 A | 1/1995 | Aoyagi | |
| 5,390,670 A | 2/1995 | Centa et al. | |
| 5,413,099 A | 5/1995 | Schmidt et al. | |
| 5,469,845 A | 11/1995 | DeLonzor et al. | |
| 5,482,036 A | 1/1996 | Diab et al. | |
| 5,483,646 A | 1/1996 | Uchikoga | |
| 5,553,614 A | 9/1996 | Chance | |
| 5,564,417 A | 10/1996 | Chance | |
| 5,575,285 A | 11/1996 | Takanashi et al. | |
| 5,611,337 A | 3/1997 | Bukta | |
| 5,630,413 A | 5/1997 | Thomas et al. | |
| 5,645,059 A | 7/1997 | Fein et al. | |
| 5,645,060 A | 7/1997 | Yorkey | |
| 5,680,857 A | 10/1997 | Pelikan et al. | |
| 5,692,503 A | 12/1997 | Keunstner | |
| 5,730,124 A | 3/1998 | Yamauchi | |
| 5,758,644 A | 6/1998 | Diab et al. | |
| 5,766,125 A | 6/1998 | Aoyagi et al. | |
| 5,779,631 A | 7/1998 | Chance | |
| 5,782,757 A | 7/1998 | Diab et al. | |
| 5,786,592 A | 7/1998 | Hök | |
| 5,807,247 A | 9/1998 | Merchant et al. | |
| 5,818,985 A | 10/1998 | Merchant et al. | |
| 5,830,136 A | 11/1998 | DeLonzor et al. | |
| 5,830,139 A | 11/1998 | Abreu | |
| 5,831,598 A | 11/1998 | Kauffert et al. | |
| 5,842,981 A | 12/1998 | Larsen et al. | |
| 5,871,442 A | 2/1999 | Madarasz et al. | |
| 5,873,821 A | 2/1999 | Chance et al. | |
| 5,891,024 A | 4/1999 | Jarman et al. | |
| 5,891,025 A | 4/1999 | Buschmann et al. | |
| 5,920,263 A | 7/1999 | Huttenhoff et al. | |
| 5,995,855 A | 11/1999 | Kiani et al. | |
| 5,995,856 A | 11/1999 | Mannheimer et al. | |
| 5,995,859 A | 11/1999 | Takahashi | |
| 5,997,343 A | 12/1999 | Mills et al. | |
| 6,011,986 A | 1/2000 | Diab et al. | |
| 6,014,576 A | 1/2000 | Raley | |
| 6,023,541 A | 2/2000 | Merchant et al. | |
| 6,064,898 A | 5/2000 | Aldrich | |
| 6,081,742 A | 6/2000 | Amano et al. | |
| 6,088,607 A | 7/2000 | Diab et al. | |
| 6,120,460 A | 9/2000 | Abreu | |
| 6,134,460 A | 10/2000 | Chance | |
| 6,150,951 A | 11/2000 | Olejniczak | |
| 6,151,107 A | 11/2000 | Schöllermann et al. | |
| 6,154,667 A | 11/2000 | Miura et al. | |
| 6,163,715 A | 12/2000 | Larsen et al. | |
| 6,165,005 A | 12/2000 | Mills et al. | |
| 6,181,958 B1 | 1/2001 | Steuer et al. | |
| 6,181,959 B1 | 1/2001 | Schöllermann et al. | |
| 6,230,035 B1 | 5/2001 | Aoyagi et al. | |
| 6,266,546 B1 | 7/2001 | Steuer et al. | |
| 6,280,381 B1 | 8/2001 | Malin et al. | |
| 6,285,895 B1 | 9/2001 | Ristolainen et al. | |
| 6,312,393 B1 | 11/2001 | Abreu | |
| 6,349,228 B1 | 2/2002 | Kiani et al. | |
| 6,353,750 B1 | 3/2002 | Kimura et al. | |
| 6,356,774 B1 | 3/2002 | Bernstein et al. | |
| 6,397,091 B2 | 5/2002 | Diab et al. | |
| 6,415,236 B2 | 7/2002 | Kobayashi et al. | |
| 6,419,671 B1 | 7/2002 | Lemberg | |
| 6,421,549 B1 | 7/2002 | Jacques | |
| 6,438,399 B1 | 8/2002 | Kurth | |
| 6,461,305 B1 | 10/2002 | Schnall | |
| 6,466,809 B1 | 10/2002 | Riley | |
| 6,487,439 B1 | 11/2002 | Skladnev et al. | |
| 6,490,466 B1 * | 12/2002 | Chew et al. | 600/323 |
| 6,501,974 B2 | 12/2002 | Huiku | |
| 6,501,975 B2 | 12/2002 | Diab et al. | |
| 6,526,301 B2 | 2/2003 | Larsen et al. | |
| 6,544,193 B2 | 4/2003 | Abreu | |
| 6,546,267 B1 | 4/2003 | Sugiura et al. | |
| 6,549,284 B1 | 4/2003 | Boas et al. | |
| 6,549,795 B1 | 4/2003 | Chance | |
| 6,571,113 B1 | 5/2003 | Fein et al. | |
| 6,580,086 B1 | 6/2003 | Schulz et al. | |
| 6,591,122 B2 | 7/2003 | Schmitt | |
| 6,594,513 B1 | 7/2003 | Jobsis et al. | |
| 6,597,933 B2 | 7/2003 | Kiani et al. | |
| 6,606,509 B2 | 8/2003 | Schmitt | |
| 6,606,511 B1 | 8/2003 | Ali et al. | |
| 6,615,064 B1 | 9/2003 | Aldrich | |
| 6,618,042 B1 | 9/2003 | Powell | |
| 6,622,095 B2 | 9/2003 | Kobayashi et al. | |
| 6,654,621 B2 | 11/2003 | Palatnik et al. | |
| 6,654,624 B2 | 11/2003 | Diab et al. | |
| 6,658,276 B2 | 12/2003 | Kianl et al. | |
| 6,658,277 B2 | 12/2003 | Wasserman | |
| 6,662,030 B2 | 12/2003 | Khalil et al. | |
| 6,668,183 B2 | 12/2003 | Hicks et al. | |
| 6,671,526 B1 | 12/2003 | Aoyagi et al. | |
| 6,671,528 B2 | 12/2003 | Steuer et al. | |
| 6,678,543 B2 | 1/2004 | Diab et al. | |
| 6,684,090 B2 | 1/2004 | Ali et al. | |
| 6,690,958 B1 | 2/2004 | Walker et al. | |
| 6,697,656 B1 | 2/2004 | Al-Ali | |
| 6,697,658 B2 | 2/2004 | Al-Ali | |
| 6,708,048 B1 | 3/2004 | Chance | |
| 6,711,424 B1 | 3/2004 | Fine et al. | |
| 6,711,425 B1 | 3/2004 | Reuss | |
| 6,714,245 B1 | 3/2004 | Ono | |
| 6,721,585 B1 | 4/2004 | Parker | |
| 6,731,274 B2 | 5/2004 | Powell | |
| 6,760,609 B2 | 7/2004 | Jacques | |
| 6,785,568 B2 | 8/2004 | Chance | |
| 6,793,654 B2 | 9/2004 | Lemberg | |
| 6,801,797 B2 | 10/2004 | Mannheimer et al. | |
| 6,801,798 B2 | 10/2004 | Geddes et al. | |
| 6,801,799 B2 | 10/2004 | Mendelson | |
| 6,829,496 B2 | 12/2004 | Nagai et al. | |
| 6,839,580 B2 | 1/2005 | Zonios et al. | |
| 6,850,053 B2 | 2/2005 | Daalmans et al. | |
| 6,863,652 B2 | 3/2005 | Huang et al. | |
| 6,873,865 B2 | 3/2005 | Steuer et al. | |
| 6,882,874 B2 | 4/2005 | Huiku | |
| 6,889,153 B2 | 5/2005 | Dietiker | |
| 6,898,451 B2 | 5/2005 | Wuori | |
| 6,939,307 B1 | 9/2005 | Dunlop | |
| 6,947,780 B2 | 9/2005 | Scharf | |
| 6,949,081 B1 | 9/2005 | Chance | |
| 6,961,598 B2 | 11/2005 | Diab | |
| 6,983,178 B2 | 1/2006 | Fine et al. | |
| 6,993,371 B2 * | 1/2006 | Kiani et al. | 600/323 |
| 6,996,427 B2 | 2/2006 | Ali et al. | |
| 6,999,904 B2 | 2/2006 | Weber et al. | |
| 7,024,235 B2 | 4/2006 | Melker et al. | |
| 7,027,849 B2 | 4/2006 | Al-Ali | |
| 7,030,749 B2 | 4/2006 | Al-Ali | |
| 7,035,697 B1 | 4/2006 | Brown | |
| 7,047,056 B2 | 5/2006 | Hannula et al. | |
| 7,127,278 B2 | 10/2006 | Melker et al. | |
| 7,142,901 B2 | 11/2006 | Kiani et al. | |
| 7,162,288 B2 | 1/2007 | Nordstrom et al. | |
| 7,162,306 B2 | 1/2007 | Caby et al. | |
| 7,209,775 B2 | 4/2007 | Bae et al. | |
| 7,236,811 B2 | 6/2007 | Schmitt | |
| 7,254,434 B2 | 8/2007 | Schulz et al. | |
| 7,263,395 B2 | 8/2007 | Chan et al. | |
| 7,272,426 B2 | 9/2007 | Schmid | |
| 7,274,955 B2 | 9/2007 | Kiani et al. | |
| 7,313,426 B2 | 12/2007 | Takeda et al. | |
| 7,313,427 B2 * | 12/2007 | Benni | 600/344 |
| 7,373,192 B2 | 5/2008 | Chew et al. | |

| | | |
|---|---|---|
| 7,373,193 B2 | 5/2008 | Al-Ali et al. |
| 7,499,740 B2 | 3/2009 | Nordstrom et al. |
| 7,500,950 B2 | 3/2009 | Al-Ali et al. |
| 7,530,949 B2 * | 5/2009 | Al Ali et al. .................. 600/300 |
| 7,844,313 B2 * | 11/2010 | Kiani et al. .................... 600/310 |
| 2001/0005773 A1 | 6/2001 | Larsen et al. |
| 2001/0020122 A1 | 9/2001 | Steuer et al. |
| 2001/0021803 A1 | 9/2001 | Blank et al. |
| 2001/0039376 A1 | 11/2001 | Steuer et al. |
| 2001/0044700 A1 | 11/2001 | Kobayashi et al. |
| 2002/0016536 A1 * | 2/2002 | Benni ........................... 600/323 |
| 2002/0026106 A1 | 2/2002 | Khalil et al. |
| 2002/0026107 A1 * | 2/2002 | Kiani et al. .................... 600/310 |
| 2002/0035318 A1 | 3/2002 | Mannheimer et al. |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0111748 A1 | 8/2002 | Kobayashi et al. |
| 2002/0133068 A1 | 9/2002 | Huiku |
| 2002/0156354 A1 | 10/2002 | Larson |
| 2002/0161287 A1 | 10/2002 | Schmitt |
| 2002/0161290 A1 | 10/2002 | Chance |
| 2002/0165439 A1 | 11/2002 | Schmitt |
| 2002/0198443 A1 | 12/2002 | Ting |
| 2003/0023140 A1 | 1/2003 | Chance |
| 2003/0055324 A1 | 3/2003 | Wasserman |
| 2003/0060693 A1 | 3/2003 | Monfre et al. |
| 2003/0139687 A1 | 7/2003 | Abreu |
| 2003/0144584 A1 | 7/2003 | Mendelson |
| 2003/0176776 A1 | 9/2003 | Huiku |
| 2003/0195402 A1 * | 10/2003 | Fein et al. ..................... 600/323 |
| 2003/0220548 A1 | 11/2003 | Schmitt |
| 2003/0220576 A1 | 11/2003 | Diab |
| 2004/0006261 A1 * | 1/2004 | Swedlow et al. .............. 600/323 |
| 2004/0010188 A1 | 1/2004 | Wasserman |
| 2004/0054270 A1 | 3/2004 | Pewzner et al. |
| 2004/0087846 A1 | 5/2004 | Wasserman |
| 2004/0107065 A1 | 6/2004 | Al-Ali |
| 2004/0127779 A1 | 7/2004 | Steuer et al. |
| 2004/0147823 A1 * | 7/2004 | Kiani et al. .................... 600/323 |
| 2004/0171920 A1 | 9/2004 | Mannheimer et al. |
| 2004/0176670 A1 | 9/2004 | Takamura et al. |
| 2004/0176671 A1 | 9/2004 | Fine et al. |
| 2004/0230106 A1 | 11/2004 | Schmitt et al. |
| 2004/0242980 A1 | 12/2004 | Kiani et al. |
| 2004/0267103 A1 * | 12/2004 | Li et al. ......................... 600/323 |
| 2005/0065417 A1 * | 3/2005 | Ali et al. ....................... 600/323 |
| 2005/0075548 A1 | 4/2005 | Al-Ali et al. |
| 2005/0080323 A1 | 4/2005 | Kato |
| 2005/0101848 A1 | 5/2005 | Al-Ali et al. |
| 2005/0101850 A1 | 5/2005 | Parker |
| 2005/0113651 A1 | 5/2005 | Wood et al. |
| 2005/0113656 A1 | 5/2005 | Chance |
| 2005/0135288 A1 | 6/2005 | Al-Ali |
| 2005/0168722 A1 | 8/2005 | Forstner et al. |
| 2005/0177034 A1 | 8/2005 | Beaumont |
| 2005/0192488 A1 | 9/2005 | Bryenton et al. |
| 2005/0203357 A1 | 9/2005 | Debreczeny et al. |
| 2005/0228248 A1 | 10/2005 | Dietiker |
| 2005/0250998 A1 | 11/2005 | Huiku |
| 2005/0267346 A1 | 12/2005 | Faber et al. |
| 2005/0283059 A1 | 12/2005 | Iyer et al. |
| 2006/0009688 A1 | 1/2006 | Lamego et al. |
| 2006/0015021 A1 | 1/2006 | Cheng |
| 2006/0020181 A1 | 1/2006 | Schmitt |
| 2006/0020185 A1 | 1/2006 | Al-Ali |
| 2006/0030763 A1 | 2/2006 | Mannheimer et al. |
| 2006/0030765 A1 * | 2/2006 | Swedlow et al. .............. 600/323 |
| 2006/0052680 A1 | 3/2006 | Diab |
| 2006/0058683 A1 | 3/2006 | Chance |
| 2006/0064024 A1 | 3/2006 | Schnall |
| 2006/0189859 A1 * | 8/2006 | Kiani et al. .................... 600/323 |
| 2006/0195024 A1 * | 8/2006 | Benni ........................... 600/323 |
| 2006/0195028 A1 | 8/2006 | Hannula et al. |
| 2006/0211925 A1 | 9/2006 | Lamego et al. |
| 2006/0217604 A1 * | 9/2006 | Fein et al. ..................... 600/323 |
| 2006/0217605 A1 * | 9/2006 | Fein et al. ..................... 600/323 |
| 2006/0217606 A1 * | 9/2006 | Fein et al. ..................... 600/323 |
| 2006/0217607 A1 * | 9/2006 | Fein et al. ..................... 600/323 |
| 2006/0217608 A1 * | 9/2006 | Fein et al. ..................... 600/323 |
| 2006/0224058 A1 | 10/2006 | Mannheimer |
| 2006/0224059 A1 * | 10/2006 | Swedlow et al. .............. 600/323 |
| 2006/0229509 A1 | 10/2006 | Al-Ali et al. |
| 2006/0229510 A1 * | 10/2006 | Fein et al. ..................... 600/323 |
| 2006/0229511 A1 * | 10/2006 | Fein et al. ..................... 600/323 |
| 2006/0247501 A1 | 11/2006 | Ali |
| 2006/0258921 A1 | 11/2006 | Addison et al. |
| 2006/0258926 A1 * | 11/2006 | Ali et al. ....................... 600/323 |
| 2007/0043269 A1 * | 2/2007 | Mannheimer et al. ......... 600/323 |
| 2007/0043270 A1 * | 2/2007 | Mannheimer et al. ......... 600/323 |
| 2007/0043271 A1 * | 2/2007 | Mannheimer et al. ......... 600/323 |
| 2007/0043272 A1 * | 2/2007 | Mannheimer et al. ......... 600/323 |
| 2007/0043273 A1 * | 2/2007 | Mannheimer et al. ......... 600/323 |
| 2007/0043274 A1 * | 2/2007 | Mannheimer et al. ......... 600/323 |
| 2007/0043275 A1 * | 2/2007 | Manheimer et al. ........... 600/323 |
| 2007/0043276 A1 * | 2/2007 | Mannheimer et al. ......... 600/323 |
| 2007/0043277 A1 * | 2/2007 | Mannheimer et al. ......... 600/323 |
| 2007/0043278 A1 * | 2/2007 | Mannheimer et al. ......... 600/323 |
| 2007/0043279 A1 * | 2/2007 | Mannheimer et al. ......... 600/323 |
| 2007/0043280 A1 * | 2/2007 | Mannheimer et al. ......... 600/331 |
| 2007/0043282 A1 * | 2/2007 | Mannheimer et al. ......... 600/336 |
| 2007/0049810 A1 * | 3/2007 | Mannheimer et al. ......... 600/323 |
| 2007/0073127 A1 | 3/2007 | Kiani et al. |
| 2007/0088207 A1 * | 4/2007 | Mannheimer et al. ......... 600/323 |
| 2007/0100220 A1 | 5/2007 | Baker, Jr. |
| 2007/0173701 A1 * | 7/2007 | Al-Ali ........................... 600/300 |
| 2007/0244376 A1 | 10/2007 | Wang |
| 2008/0015424 A1 * | 1/2008 | Bernreuter ..................... 600/323 |
| 2008/0081969 A1 | 4/2008 | Feldman et al. |
| 2008/0081970 A1 | 4/2008 | Boyce et al. |
| 2008/0097175 A1 | 4/2008 | Boyce et al. |
| 2008/0221462 A1 | 9/2008 | Baker, Jr. |
| 2008/0316488 A1 | 12/2008 | Mao et al. |
| 2009/0182209 A1 * | 7/2009 | Benni ........................... 600/323 |
| 2009/0234207 A1 * | 9/2009 | Rantala ......................... 600/323 |
| 2009/0281403 A1 * | 11/2009 | Benni ........................... 600/331 |
| 2010/0049018 A1 * | 2/2010 | Duffy et al. ................... 600/323 |
| 2010/0312079 A1 * | 12/2010 | Larsen et al. ................. 600/323 |

FOREIGN PATENT DOCUMENTS

| | | |
|---|---|---|
| EP | 1828731 A1 | 6/2006 |
| JP | 3124073 | 5/1991 |
| JP | 3170866 | 7/1991 |
| JP | 3238813 | 10/1991 |
| JP | 4332536 | 11/1992 |
| JP | 5049625 | 3/1993 |
| JP | 7124138 | 5/1995 |
| JP | 2003194714 | 7/2003 |
| JP | 2003210438 | 7/2003 |
| JP | 2004008572 | 1/2004 |
| JP | 2004113353 | 4/2004 |
| JP | 2004194908 | 7/2004 |
| JP | 2004248819 | 9/2004 |
| JP | 2004290545 | 10/2004 |
| JP | 25087405 A2 | 4/2005 |
| JP | 3818211 B2 | 9/2006 |
| JP | 27020836 A2 | 2/2007 |
| WO | WO9111137 | 8/1991 |
| WO | WO9200513 | 1/1992 |
| WO | WO9309711 | 5/1993 |
| WO | WO93/16629 | 9/1993 |
| WO | WO9843071 | 10/1998 |
| WO | WO9932030 | 7/1999 |
| WO | WO0021438 | 4/2000 |
| WO | 2006124455 A1 | 11/2006 |

OTHER PUBLICATIONS

Buschman, J.P., et al.; "Principles and Problems of Calibration of Fetal Oximeters," Biomedizinische Technik, vol. 42, pp. 265-266 (1997).

Leahy, Martin J., et al.; "Sensor Validation in Biomedical Applications," IFAC Modelling and Control in Biomedical Systems, Warwick, UK; pp. 221-226 (1997).

East, Christine E., et al.; "Fetal Oxygen Saturation and Uterine Contractions During Labor," American Journal of Perinatology, vol. 15, No. 6, pp. 345-349 (Jun. 1998).

Edrich, Thomas, et al.; "Can the Blood Content of the Tissues be Determined Optically During Pulse Oximetry Without Knowledge of the Oxygen Saturation?—An In-Vitro Investigation," Proceedings of the 20th Annual International conference of the IEEE Engie in Medicine and Biology Society, vol. 20, No. 6, p. 3072-3075, 1998.

Such, Hans Olaf; "Optoelectronic Non-invasive Vascular Diagnostics Using multiple Wavelength and Imaging Approach," Dissertation, (1998).

Todd, Bryan, et al.; "The Identification of Peaks in Physiological Signals," Computers and Biomedical Research, vol. 32, pp. 322-335 (1999).

Coetzee, Frans M.; "Noise-Resistant Pulse Oximetry Using a Synthetic Reference Signal," IEEE Transactions on Biomedical Engineering, vol. 47, No. 8, Aug. 2000, pp. 1018-1026.

Goldman, Julian M.; "Masimo Signal Extraction Pulse Oximetry," Journal of Clinical Monitoring and Computing, vol. 16, pp. 475-483 (2000).

Kaestle, S.; "Determining Artefact Sensitivity of New Pulse Oximeters in Laboratory Using Signals Obtained from Patient," Biomedizinische Technik, vol. 45 (2000).

Belal, Suliman Yousef, et al.; "A fuzzy system for detecting distorted plethysmogram pulses in neonates and paediatric patients," Physiol. Meas., vol. 22, pp. 397-412 (2001).

Cysewska-Sobusaik, Anna; "Metrological Problems With noninvasive Transillumination of Living Tissues," Proceedings of SPIE, vol. 4515, pp. 15-24 (2001).

Maletras, Francois-Xavier, et al.; "Construction and calibration of a new design of Fiber Optic Respiratory Plethysmograph (FORP)," Optomechanical Design and Engineering, Proceedings of SPIE, vol. 4444, pp. 285-293 (2001).

Chan, K.W., et al.; "17.3: Adaptive Reduction of Motion Artifact from Photoplethysmographic Recordings using a Variable Step-Size LMS Filter," IEEE, pp. 1343-1346 (2002).

Lutter, N., et al.; "Accuracy of Noninvasive Continuous Blood Pressure; Measurement Utilising the Pulse Transit Time," Journal of clinical Monitoring and Computing, vol. 17, Nos. 7-8, pp. 469 (2002).

Relente, A.R., et al.; "Characterization and Adaptive Filtering of Motion Artifacts in Pulse Oximetry using Accelerometers," Proceedings of the Second joint EMBS/BMES Conference, Houston, Texas, Oct. 23-26, 2002; pp. 1769-1770.

Cyrill, D., et al.; "Adaptive Comb Filter for Quasi-Periodic Physiologic Signals," Proceedings of the 25th Annual International Conference of the IEEE EMBS, Cancun, Mexico, Sep. 17-21, 2003; pp. 2439-2442.

A. Johansson; "Neural network for photoplethysmographic respiratory rate monitoring," Medical & Biological Engineering & Computing, vol. 41, pp. 242-248 (2003).

Lee, C.M., et al.; "Reduction of motion artifacts from photoplethysmographic recordings using wavelet denoising approach," IEEE EMBS Asian-Pacific Conference on Biomedical Engineering, Oct. 20-22, 2003; pp. 194-195.

Stetson, Paul F.; "Determining Heart Rate from Noisey Pulse Oximeter Signals Using Fuzzy Logic," The IEEE International Conference on Fuzzy Systems, St. Louis, Missouri, May 25-28, 2003; pp. 1053-1058.

Lopez-Silva, S.M., et al.; "Transmittance Photoplethysmography and Pulse Oximetry With Near Infrared Laser Diodes," IMTC 2004—Instrumentation and Measurement Technology Conference, Como, Italy, May 18-20, 2004; pp. 718-723.

Addison, Paul S., et al.; "A novel time-frequency-based 3D Lissajous figure method and its application to the determination of oxygen saturation from the photoplethysmogram," Institute of Physic Publishing, Meas. Sci. Technol., vol. 15, pp. L15-L18 (2004).

Hamilton, Patrick S., et al.; "Effect of Adaptive Motion-Artifact Reduction on QRS Detection," Biomedical Instrumentation & Technology, pp. 197-202 (undated), Provided on Apr. 30, 2009.

J. Huang, et al.; "Low Power Motion Tolerant Pulse Oximetry," Abstracts, A7, p. S103. (undated), Provided on Apr. 30, 2009.

Kim, J.M., et al.; "Signal Processing Using Fourier & Wavelet Transform," pp. II-310-II-311 (undated), Provided on Apr. 30, 2009.

R. Neumann, et al.; "Fourier Artifact suppression Technology Provides Reliable SpO2,," Abstracts, A11, p. S105. (undated), Provided on Apr. 30, 2009.

Odagiri, Y.; "Pulse Wave Measuring Device," Micromechatronics, vol. 42, No. 3, pp. 6-11 (undated) (Article in Japanese—contains English summary of article), Provided on Apr. 30, 2009.

* cited by examiner

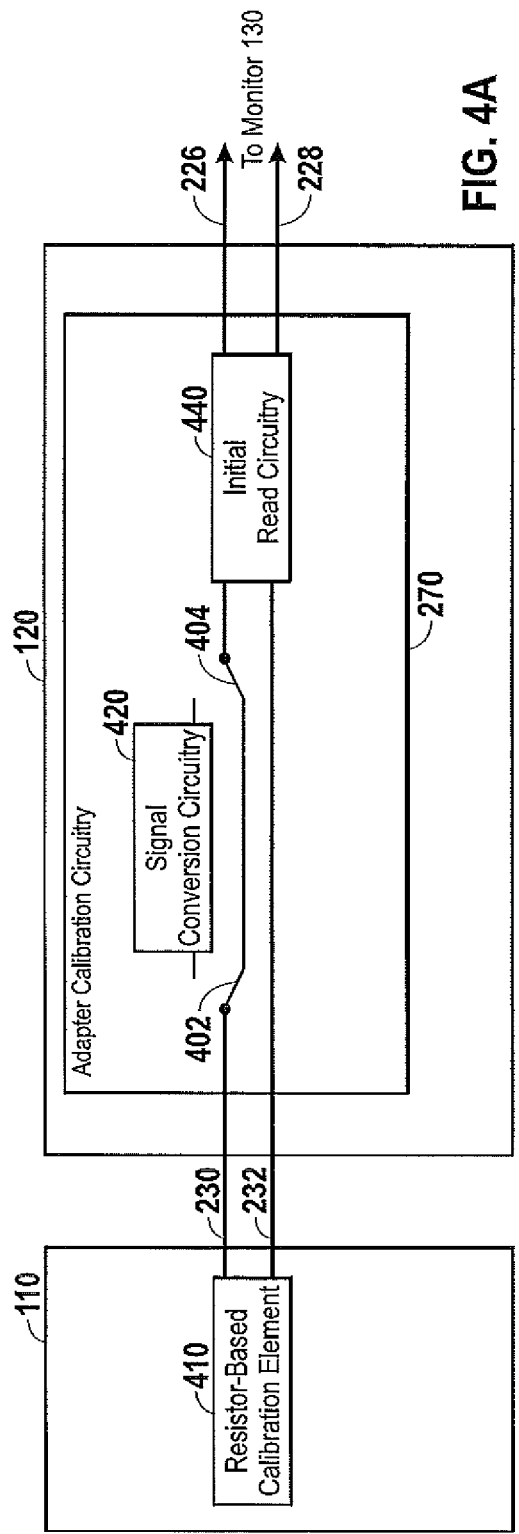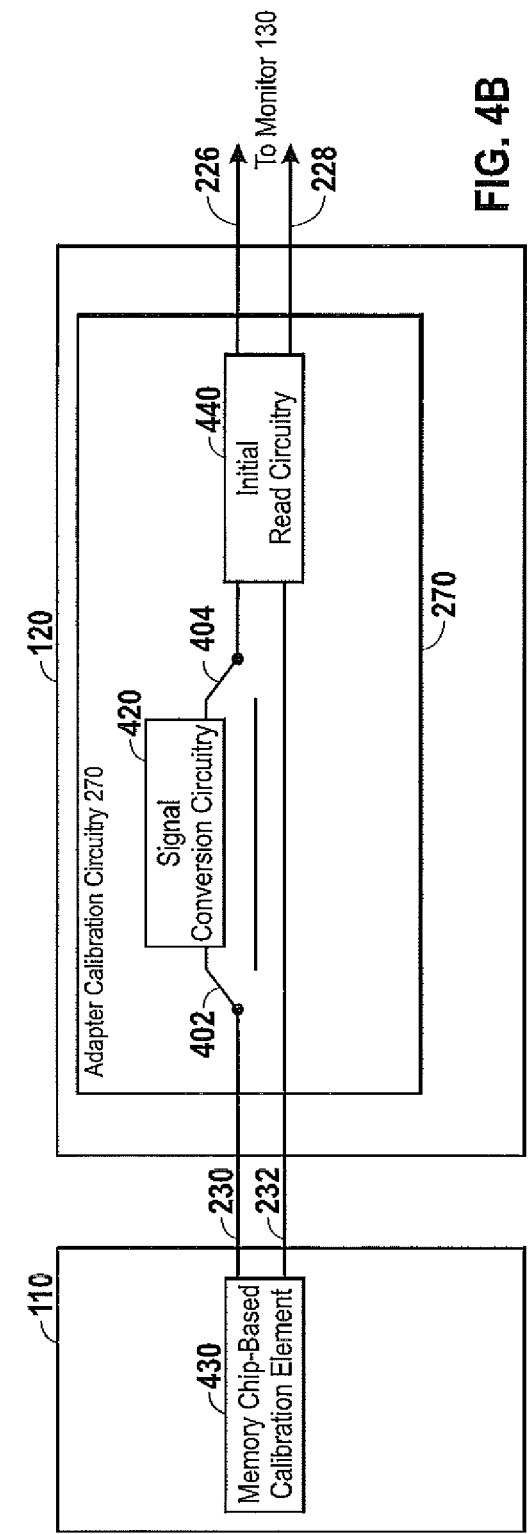

SYSTEM AND METHOD FOR FACILITATING SENSOR AND MONITOR COMMUNICATION

CROSS-REFERENCE TO RELATED APPLICATION

This claims the benefit of U.S. Provisional Patent Application No. 61/072,598, filed Mar. 31, 2008, which is hereby incorporated by reference herein in its entirety.

BACKGROUND

The present disclosure relates generally to pulse oximetry and, more specifically, to an adapter for connecting oximeter sensors with oximeter monitors.

This section is intended to introduce the reader to various aspects of art that may be related to various aspects of disclosed embodiments, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of healthcare, caregivers (e.g., doctors and other healthcare professionals) often desire to monitor certain physiological characteristics of their patients. Accordingly, a wide variety of monitoring devices have been developed for monitoring many such physiological characteristics. These monitoring devices often provide doctors and other healthcare personnel with information that facilitates provision of the best possible healthcare for their patients. As a result, such monitoring devices have become a perennial feature of modern medicine.

One method for monitoring physiological characteristics of a patient is commonly referred to as pulse oximetry, and the devices built based upon pulse oximetry methods are commonly referred to as pulse oximeters. Pulse oximeters may be used to measure and monitor various blood flow characteristics of a patient. For example, a pulse oximeter may be utilized to monitor the blood oxygen saturation of hemoglobin in arterial blood ($SpO_2$), the volume of individual blood pulsations supplying the tissue, and/or the rate of blood pulsations corresponding to each heartbeat of a patient. In fact, the "pulse" in pulse oximetry refers to the time-varying amount of arterial blood in the tissue during each cardiac cycle.

In general, monitoring systems, such as pulse oximetry systems, include a sensor and a monitor. The sensor collects data that is transmitted to the monitor for analysis. For example, pulse oximeters typically utilize a non-invasive sensor that is placed on or against a patient's tissue that is well perfused with blood, such as a patient's finger, toe, forehead or earlobe. The pulse oximeter sensor emits light and photoelectrically senses the light after passage through the perfused tissue. The sensor then transmits data relating to the sensed light to the monitor. The light emitted by the sensor is typically selected to include one or more wavelengths that are absorbed or scattered in an amount related to the presence of oxygenated versus de-oxygenated hemoglobin in the blood. Thus, data collected by the sensor relating to detected light may be used by a pulse oximeter to calculate one or more of the above-referenced physiological characteristics based upon the absorption or scattering of the light. For example, a monitor may use a determination of the amount of light absorbed and/or scattered, as detected by the sensor, to estimate an amount of oxygen in the tissue using various algorithms.

The sensors and monitors of typical monitoring systems, such as pulse oximeter systems, are often specifically configured to communicate with one another. For example, a sensor may be specifically configured to operate with a particular type of monitor. Indeed, if a sensor and a monitor are not specifically designed to cooperate, they may not function together. This can be an issue when upgrades are available for a sensor or monitor. For example, it may be desirable to utilize a new sensor that includes upgraded technology because it provides better performance and the upgraded technology is more affordable. However, older monitors, which can be expensive to replace, may not be able to take advantage of the improved sensor technology because they are not compatible with the updated technology.

SUMMARY

Certain aspects commensurate in scope with this disclosure are set forth below. It should be understood that these aspects are presented merely to provide the reader with a brief summary of certain embodiments of the disclosure and that these aspects are not intended to limit the scope of embodiments of the disclosure. Indeed, embodiments of the disclosure may encompass a variety of aspects that may not be set forth below.

According to an embodiment, there may be provided an adapter including communications circuitry configured to facilitate communication with an oximeter sensor, communications circuitry configured to facilitate communication with an oximeter monitor, and calibration circuitry configured to receive calibration information in a first form from the oximeter sensor and to convert the calibration information into a second form which is readable by the oximeter monitor.

According to an embodiment, there may also be provided a pulse oximetry system including an oximeter sensor, an oximeter monitor, and an adapter configured to receive calibration information in a first form from the oximeter sensor and to convert the calibration information into a second form which the oximeter monitor is capable of reading.

Finally, according to an embodiment, there may be provided a method for communicating calibration information from an oximeter sensor to an oximeter monitor including determining a type of calibration element present within the oximeter sensor, enabling calibration signal conversion circuitry within the adapter if the calibration element is a digital memory chip, and sending a message to the oximeter monitor to begin receiving oximetry data from the oximeter sensor.

BRIEF DESCRIPTION OF THE DRAWINGS

These and other features, aspects, and advantages of this disclosure may become better understood when the following detailed description of certain exemplary embodiments is read with reference to the accompanying drawings in which like characters represent like parts throughout the drawings, wherein:

FIGS. 4A and 4B are block diagrams of a pulse oximeter sensor and adapter in accordance with an embodiment.

Figure 1:
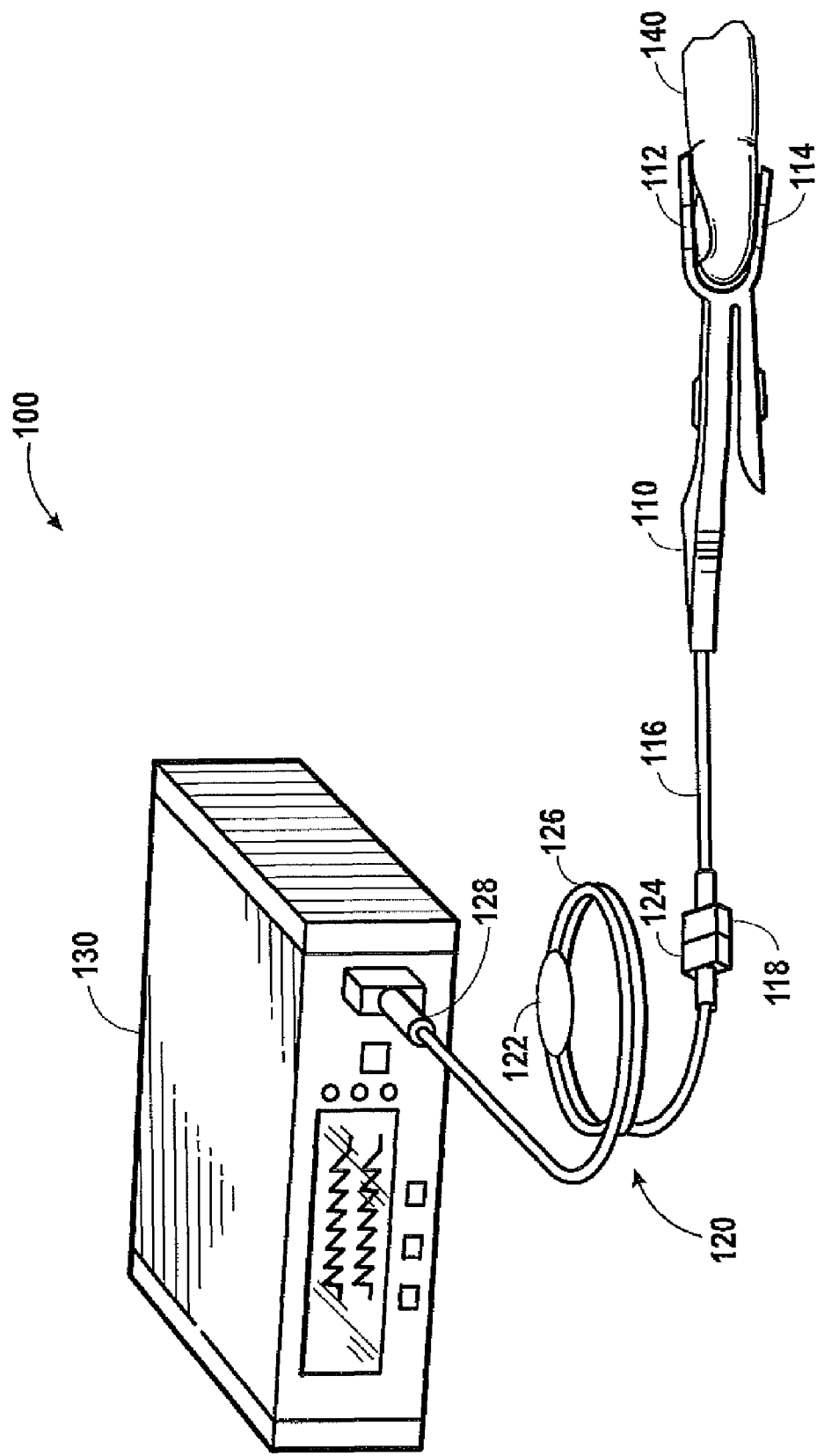
FIG. 1 is a perspective view of a pulse oximetry system in accordance with an embodiment.

While the present disclosure is susceptible to various modifications and alternative forms, specific exemplary embodiments thereof have been shown in the drawings and are herein described in detail. It should be understood, however, that the description herein of specific exemplary embodiments is not intended to limit the disclosure to the particular forms disclosed herein, but to the contrary, this disclosure is to cover all modifications and equivalents as defined by the appended claims.

DETAILED DESCRIPTION

Various embodiments will be described below. These described embodiments are only exemplary of the present disclosure. Additionally, in an effort to provide a concise description of these exemplary embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present methods and systems generally relate to physiological monitoring instruments and, in particular, to systems and devices that cooperate with sensors that include a mechanism for storing and providing a monitor with data relating to measurement of a physiological characteristic. Embodiments of the present disclosure may include pulse oximetry sensors that include coded information relating to use of the sensors (e.g., a value associated with interpreting data from the sensor). Pulse oximetry systems are discussed below as examples to facilitate detailed discussion of present embodiments. However, the methods and systems discussed below are merely examples, and present embodiments are not limited to pulse oximetry devices. Indeed, some embodiments may be extended to various other physiological monitoring instruments.

In accordance with an embodiment, blood oxygen saturation, commonly denoted as $SpO_2$, may be estimated as a ratio of oxygenated hemoglobin ($HbO_2$) to deoxygenated hemoglobin (Hb) present in a patient's tissue. Hemoglobin is the component of blood which transports oxygen throughout the body. The ratio of $HbO_2$ to Hb can be determined by shining light at certain wavelengths into a patient's tissue and measuring the absorbance of the light. In an embodiment, a first wavelength may be selected at a point in the electromagnetic spectrum where the absorption of $HbO_2$ differs from the absorption of reduced Hb, and a second wavelength may be selected at a different point in the spectrum where the absorption of Hb and $HbO_2$ differs from those at the first wavelength. For example, wavelength selections for measuring normal blood oxygenation levels typically include a red light emitted at approximately 660 nm and a near-infrared light emitted at approximately 900 nm.

One method for estimating $SpO_2$ is to calculate a characteristic known as the ratio-of-ratios (Ratrat) of the absorption of red light (RED) to near-infrared light (IR). While various methods may be utilized to calculate Ratrat, in one method in accordance with an embodiment, a sensor is used to emit red and near-infrared light into a patient's tissue and detect the light that is reflected back. Signals indicative of the detected light are conditioned and processed to generate plethysmographic waveforms having generally sinusoidal shape, having both an alternating current (AC) and a direct current (DC) component. The AC and DC components of the RED wavelength and IR wavelength signals may then be used to calculate Ratrat, which has been observed to correlate well to $SpO_2$. This observed correlation may be used to estimate $SpO_2$ based on the measured value of the Ratrat.

Therefore, pulse oximeters may precisely measure Ratrat in order to determine $SpO_2$. The relationship between Ratrat and $SpO_2$ may follow a smooth line that serves as a sensor calibration curve. Because the light absorption of the blood's $HbO_2$ and Hb is significantly wavelength-dependent, the relationship between Ratrat and $SpO_2$ may depend heavily upon the specific wavelength emissions of the sensor's light emitting diodes (LEDs). For instance, if the red LED emits at 640 nm as opposed to 660 nm, the light absorption of the blood may increase compared to a truly red emitter. The result may be that the sensor's calibration curve would be shifted and rotated to a certain degree.

Therefore, more accurate measurements of $SpO_2$ may be taken when the sensor's calibration curve corresponds to the actual wavelengths of the sensor's LEDs. For this reason, pulse oximeter manufacturers may identify the emitted wavelengths in order to achieve accurate readings. Many manufacturers identify an LED wavelength range for a particular sensor and program a corresponding calibration curve into a pulse oximetry monitor that corresponds to this LED wavelength range. To do so, these manufacturers may use a resistor-encoding scheme in which several calibration curves are programmed into pulse oximeters to span a broad range of LED wavelengths.

This resistor calibration method, which may be abbreviated as RCAL™ in systems manufactured by the present assignee, communicates to the monitor which curves should be used. When the sensor is connected to the monitor, a resistor within the sensor may be read by the monitor to identify specifically which of the pre-programmed curves should be used to calculate $SpO_2$ values. During the manufacturing of each sensor, the wavelength characteristics of the red and infrared LEDs may be measured and an appropriate resistor may be installed in the sensor. The RCAL™ system may be used by the monitor to identify from a lookup table (e.g., Table 1) which of the pre-programmed curves should be used based on the specific resistor values.

TABLE 1

Example RCAL ™ Lookup Values

| RCAL ™ Resistor (Ω) | Calibration Curve |
|---|---|
| 1000 | Curve #1 |
| 2000 | Curve #2 |
| 3000 | Curve #3 |
| . . . | . . . |
| N,000 | Curve #N |

However, predefining calibration curves to address LED wavelength variations can be an issue for several reasons. First, pulse oximetry manufacturers may not be able to take advantage of newer high-efficiency LEDs because their spectral properties may be different from those designed by semiconductor companies years ago. Newer LEDs can reduce power needs of oximeters, leading to longer battery life. In addition, newer LEDs can dramatically increase signal strength, improving monitoring performance. Therefore, as newer LEDs become available, oximeter manufacturers may want to be able to take advantage of the latest advancements in LED technology. Second, oximeter manufacturers may be constrained and unable to implement new sensor designs when the new designs do not precisely conform to the pre-programmed calibration curves in the monitors. Having to fit new sensors into the available choices of calibration curves may limit the possibilities for new sensor designs. Finally, many RCAL™ calibration curves were created in the mid-1980s, based on LEDs and sensor designs of that time. New sensors developed since then have had to conform to these pre-programmed curves to ensure compatibility across the installed base of oximeter monitors.

In response to these issues, new oximeter systems have been developed to provide for greater sensor and monitor performance while at the same time accommodating future sensor designs as patient care evolves. One such system accomplishes these objectives by incorporating a small digital memory chip within the sensor. Each digital memory chip may be programmed with the full calibration information for that sensor, along with any other sensor-specific data the oximeter can use to enhance performance. This design allows manufacturers to develop sensors that address specific clinical needs without being hampered by the earlier sensor calibration constraints.

This type of system still utilizes calibration. However, instead of having to fit within the pre-programmed curves within oximeter monitors, sensors with digital memory chips may hold their individual calibration curves in memory. As such, each sensor may be programmed with specific coefficients which define its calibration curve. Therefore, manufacturers can now store within the chip any calibration curve needed, whether for current sensor designs or for those created in the future. Because new calibration curves can be developed as needed, manufacturers can design new sensors with improved performance without the constraints of the past.

Though existing oximeter monitors could conceivably be re-programmed with additional curves, the process for doing so could prove very difficult, particularly when the large numbers of installed monitors around the world is taken into account. Building digital memory chips within sensors allows for integrating new sensor calibration curves without the hassle of updating oximeter monitors. Therefore, implementing upgrades through sensors, rather than monitors, may prove more cost effective and efficient.

In addition, the memory chip may provide room for additional sensor-specific operating parameters to be stored within the sensor. For example, the model name of the sensor being stored, and model-specific troubleshooting tips may be provided. However, despite all of the advantages created by building a memory chip into the sensors, one major disadvantage may be created—the fact that oximeter monitors may not inherently be able to communicate with the sensors. Indeed, whereas older monitors may be expecting an encoded signal via a resistor, they may now be interfacing with a chip holding the calibration curve in memory. Conversely, when newer monitors are expecting to interface with a memory chip, they may experience only a resistor element in an older sensor. Therefore, it is now recognized that it would be advantageous to have an adapter which can modify the sensor signals accordingly.

FIG. 1 is a perspective view of a pulse oximetry system in accordance with an embodiment. The pulse oximetry system is generally indicated by reference numeral 100. The system 100 may include a sensor 110, an adapter 120, and a monitor 130 which cooperate to detect and analyze patient characteristics. In the illustrated embodiment, the monitor 130 couples via the adapter 120 to the sensor 110 that is applied to a patient 140. More specifically, the sensor 110 may be configured to detect and transmit signals to the monitor 130 via the adapter 120. The signals transmitted by the sensor 110 may be indicative of $SpO_2$ levels in the patient's 140 tissue. The adapter 120 may convert the signals from the sensor 110 into a form that is readable by the monitor 130. For example, the monitor may be configured to receive information from the sensor 110 relating to a resistance value (for calibration purposes) whereas the sensor 110 may be configured to transmit information to the monitor 130 relating to values read from a memory feature of the sensor 110.

In the illustrated embodiment, the sensor 110 includes a pair of LEDs 112, a photo detector 114, a sensor cable 116, and a sensor connecting plug 118. In FIG. 1, the sensor 110 is shown as a clip-on sensor. However, present embodiments can be applied to many sensor implementations, including those attached to a patient by adhesive and other attachment means. Light from the LEDs 112 at two different wavelengths (e.g., red and infrared) may be transmitted through a patient's blood perfused tissues (e.g., in a finger) and detected by the photo detector 114. Selection of the wavelengths of the LEDs 112 may be based on a number of factors. Such factors may include the absorption characteristics of the patient and transmission medium. The detected optical signal from the photo detector 114 may then be provided to the monitor 130 for processing.

The sensor 110 may be connected to the sensor cable 116. In the illustrated embodiment, the sensor cable 116 is directly connected to the adapter 120 via the sensor connecting plug 118. However, as will be appreciated by those in the art, the sensor 110 may also be connected directly to the monitor 130 (e.g., in instances where the sensor 110 is compatible with the monitor 130). In addition, in other embodiments, the sensor 110 may be configured to connect wirelessly with the adapter 120 and/or the monitor 130, obviating the need for the sensor cable 116 and sensor connecting plug 118.

Also, in the illustrated embodiment, the adapter 120 includes an adapter body 122, an adapter-to-sensor connecting plug 124, an adapter cable 126, and an adapter-to-monitor connecting plug 128. The adapter body 122 may contain all of the circuitry required to convert the signals from the sensor 110 into a form that is readable by the monitor 130. The adapter 120 may be directly connected to the sensor 110 via the adapter-to-sensor connecting plug 124 and adapter cable 126. Similarly, the adapter may be connected to the monitor 130 via the adapter-to-monitor connecting plug 128 and adapter cable 126. In addition, in other embodiments, the adapter 120 may be configured to connect wirelessly with the sensor 110 and/or the monitor 130, obviating the need for the adapter cable 126 and adapter connecting plugs 124, 128. Also, the adapter 120 may have a self-contained power source (e.g., rechargeable battery) within the adapter body 122, plug into a power outlet directly (using electrical cords not shown), or derive its power from the monitor 130.

In the illustrated embodiment, the monitor 130 may be a pulse oximeter, such as those available from Nellcor Puritan Bennett LLC and/or Covidien, or may be another monitor for measuring other body-related metrics using spectrophotometric and/or other methods. Additionally, the monitor 130 may be a multi-purpose monitor suitable for performing pulse oximetry and measurement of other combinations of physiological and/or biochemical monitoring processes, using data acquired via the sensor 110.

The adapter 120 has been described for use in combination with a sensor 110 and a monitor 130 wherein the monitor 130 performs the signal processing of the detected signal and compression of the processed data. In another embodiment, the adapter 120 may be configured to process (and compress, if necessary or desirable) the detected signal. This embodiment allows for independent operation of the sensor 110 and adapter 120 without support from a monitor 130. The data stored within the sensor 110 and adapter 120 may be provided to a monitor 130 for display. The amount of signal processing and compression that can be achieved by circuitry within the adapter 120 may be primarily limited by the available technology, which inevitably improves over time. In the near term, physiological data that does not require extensive signal processing and compression (e.g., temperature, peak amplitude in a waveform, heart rate, and so on) can be collected and stored by the adapter 120.

Figure 2:
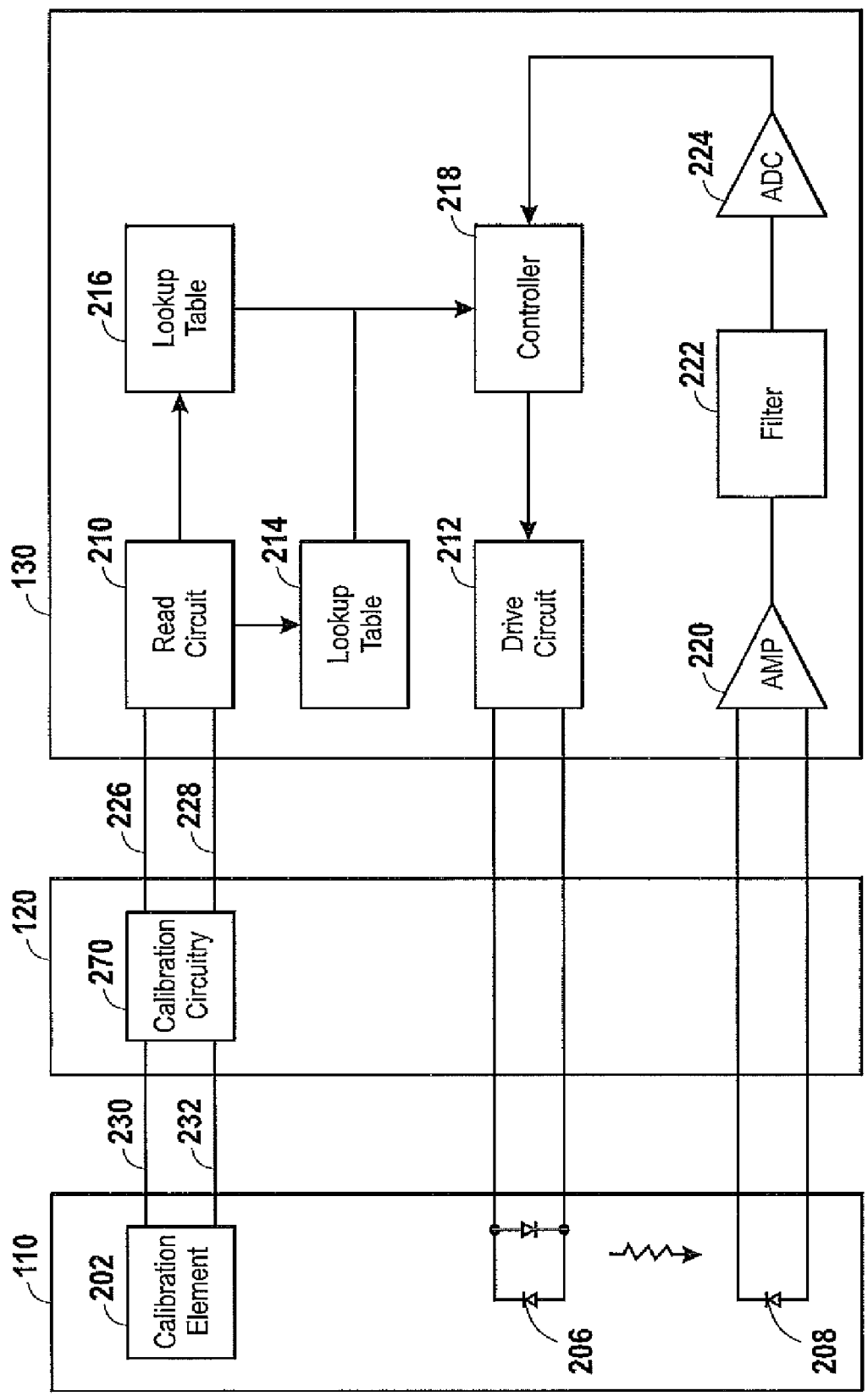
FIG. 2 is a block diagram of a pulse oximeter monitor, adapter, and sensor in accordance with an embodiment.

FIG. 2 is a block diagram of a pulse oximeter system incorporating a calibration element 202 within the sensor 110 in accordance with an embodiment. In one embodiment, the calibration element 202 may be a two-lead semiconductor digital memory chip. The calibration element 202 may be part of the sensor 110 which also includes red and infrared LEDs 206, along with a photo detector 208. If desired, the LEDs 206 may be replaced with other light emitting elements such as lasers.

The oximeter monitor 130 may include a read circuit 210, a drive circuit 212, lookup tables 214 and 216, a controller 218, an amplifier 220, a filter 222, and an analog-to-digital converter 224. The read circuit 210 may be provided for reading multiple coded values across the two leads 226, 228 connected to the adapter calibration circuitry 270 which may in turn be connected to the calibration element 202 via two other leads 230, 232. One value may be provided to a lookup table 214 to determine appropriate wavelength-dependent coefficients for the oxygen calculation. The other value(s) may then be provided to another lookup table(s) 216 which provides input (e.g., coefficients) to other calculations performed by the controller 218. The controller 218 may provide signals to a drive circuit 212 to control the amount of drive current provided to the LEDs 206.

The photo detector 208 may be connected through the amplifier 220 and the filter 222 to the A/D converter 224. This forms a feedback path used by the controller 218 to adjust the drive current to optimize the intensity range of the signal received. For example, the signal may be within the analog range of the circuits employed. The signal may also be within the range of the A/D converter 224. For example, one rule that may be applied is to adjust LED drives and amplifier gains so that both red and IR signals fall between 40% and 80% of full scale reading of the A/D converter 224.

If the sensor 110 is the type that uses the RCAL™ calibration method, leads 226 and 228 of the sensor 110 may be connected directly to leads 230 and 232 of the monitor 130. As such, after connecting the sensor 110 to the monitor 130, the read circuit 210 may read an analog voltage which corresponds to the RCAL™ resistor value of the sensor 110. This voltage may then be applied to an A/D converter (not shown) to provide a value which can be used to index into the lookup table 214. Conversely, certain issues may arise if the monitor 130 is configured to communicate with a sensor 110 which uses the RCAL™ calibration method but, instead, the sensor 110 uses a digital memory chip for calibration purposes.

However, in an embodiment, the adapter 120 contains adapter calibration circuitry 270 which is connected between the pairs of leads 226, 228 and 230, 232. As such, the adapter calibration circuitry 270 may be responsible for converting signals sent to/from the read circuit 210 such that both older sensors (using resistors for calibration) and newer sensors (using digital memory chips for calibration) may be compatible with monitors configured to operate with sensors that use resistors for calibration. As will be appreciated by one skilled in the art, the methods described below for implementing an adapter 120 may also be applied to other situations. More specifically, similar methods may be used within the adapter calibration circuitry 270 such that both older sensors (using resistors for calibration) and newer sensors (using digital memory chips for calibration) may be compatible with monitors configured to connect to sensors which use digital memory chips for calibration. In either case, signals sent to/from the read circuit 210 may be converted from a first form to a second form with which the monitor 130 is configured to operate.

One objective of the adapter calibration circuitry 270 is to ensure that the monitor 130 responds in the same manner when either type of sensor—one that uses a resistor for calibration or one that uses a memory chip for calibration—is in communication with the monitor 130 via the adapter 120. This can be accomplished using any number of methods and features, a few of which will be described below. However, it should be understood that these disclosed embodiments are not intended to be limited to the particular methods and features disclosed below.

Figure 3:
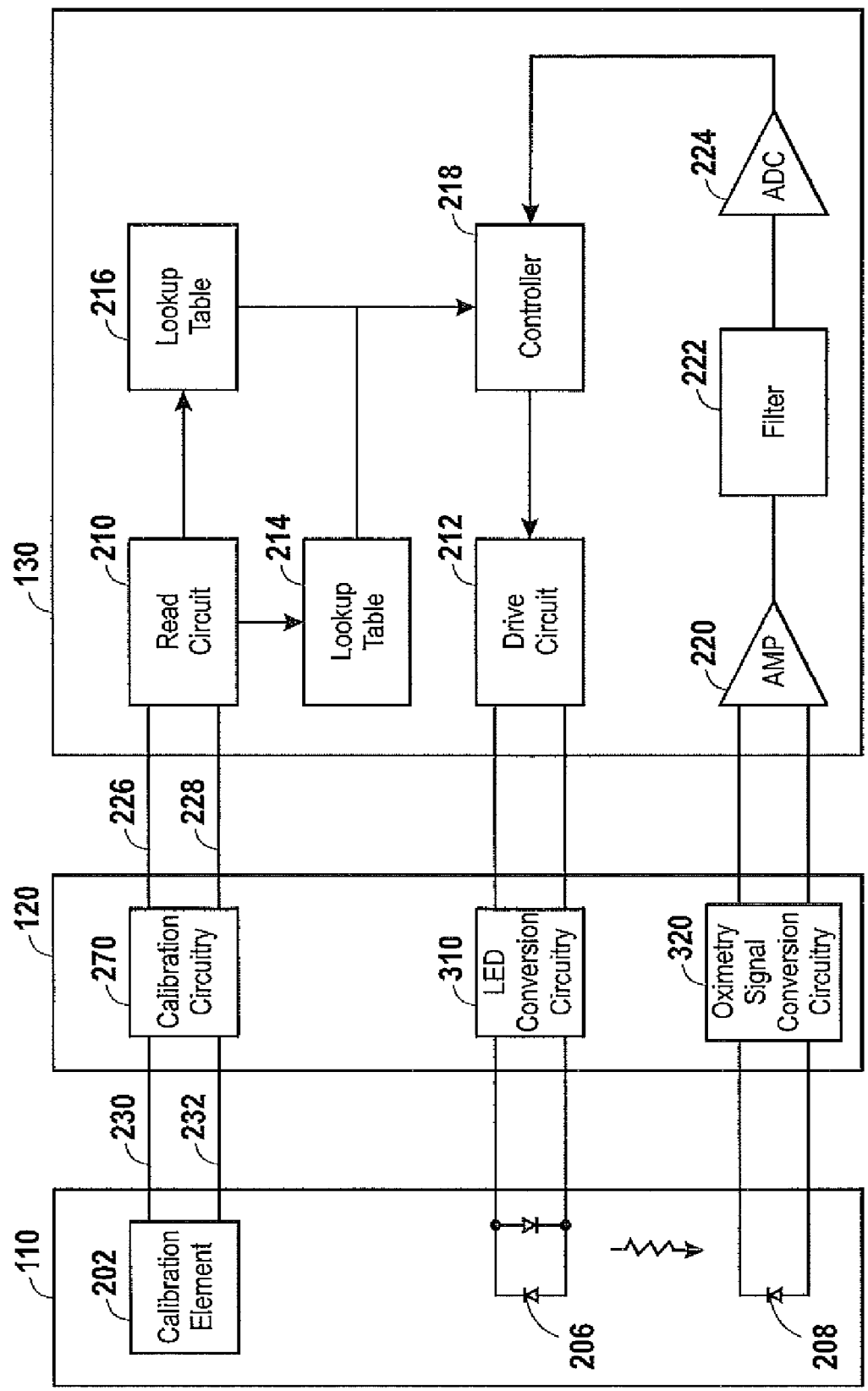
FIG. 3 is a block diagram of a pulse oximeter monitor, adapter, and sensor incorporating LED and oximetry signal conversion circuitry in accordance with an embodiment.

FIG. 3 is a block diagram of a pulse oximeter system incorporating LED and oximetry signal conversion circuitry 310, 320 in accordance with an embodiment. In addition to converting signals relating to sensor calibration, the adapter 120 may also be used for conversion of LED signals to the sensor 110 and oximetry signals from the sensor 110. For instance, in response to information gathered from the memory chip in the sensor 110 (e.g., either calibration information or any other information stored in the memory chip), either the LED signals or returning oximetry signals may be modified and/or pre-conditioned to take into account particular characteristics of the sensor 110. In addition, the adapter LED conversion circuitry 310 and/or the oximetry signal conversion circuitry 320 may simply be used to offload some of the functionality of the monitor 130, depending on the circumstances.

FIGS. 4A and 4B are block diagrams of the adapter 120 and the sensor 110 in accordance with various embodiments. In these embodiments, the adapter calibration circuitry 270 may contain switches 402, 404 enabling two alternate modes of operation for the adapter 120. FIG. 4A illustrates the first mode of operation, where the adapter 120 is connected to the sensor 110 employing a resistor-based calibration element 410. In this situation, there is no need to use the calibration signal conversion circuitry 420. Therefore, it may be bypassed and the signal from the resistor-based calibration element 410 may simply be passed along through the adapter calibration circuitry 270 to the monitor 130. Conversely, FIG. 4B illustrates the second mode of operation, where the adapter 120 is connected to the sensor 110 employing a memory chip-based calibration element 430. In this situation, the calibration signal conversion circuitry 420 is needed and, therefore, should not be bypassed. In both situations, initial read circuitry 440 will most likely be used to ensure that switches 402, 404 are toggled appropriately upon connecting the sensor 110, the adapter 120, and the monitor 130 so that the read circuit 210 of the monitor 130 is able to process the signals returned by the sensor 110 via the adapter 120.

Figure 5:
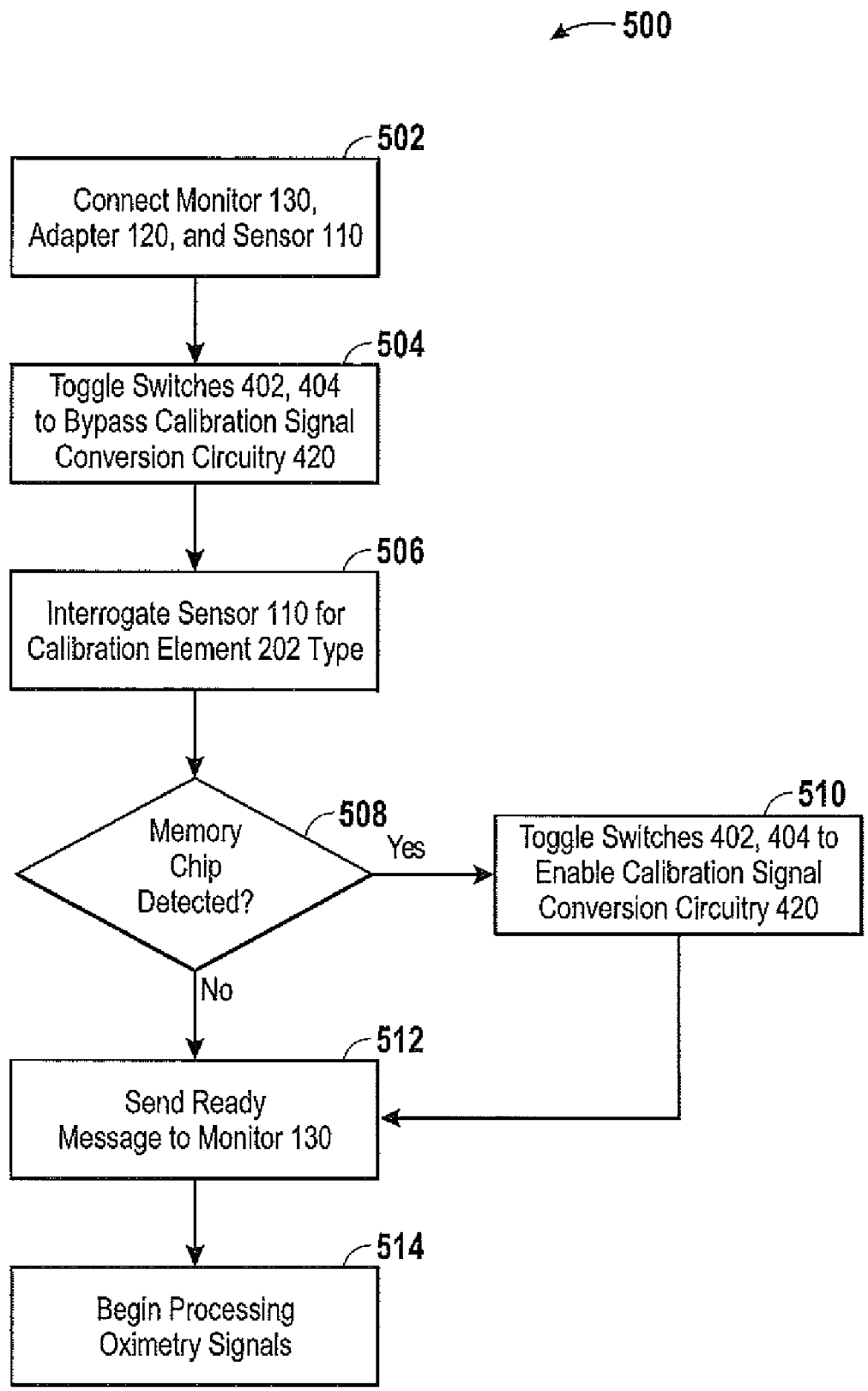
FIG. 5 is a flowchart illustrating a method for initializing the signal conversion circuitry of an oximeter adapter in accordance with an embodiment.

FIG. 5 shows an embodiment of a method for initializing the calibration signal conversion circuitry 420 of the adapter 120. Initially, the monitor 130, the adapter 120, and the sensor 110 may be connected to one another, as indicated by block 502. Upon detecting connection, the initial read circuitry 440 may toggle the switches 402, 404 (block 504) to bypass the calibration signal conversion circuitry 420. Clearing the connection between the adapter 120 and the sensor 110 allows for the initial read circuitry 440 to interrogate (block 506) the sensor 110 in order to establish what type of calibration element 202 is being used by the sensor 110.

At this point, a determination may be made (block 508) by the initial read circuitry 440 of whether a memory chip is used in sensor 110 for calibration purposes. This may be determined, for instance by attempting to access a particular value from a memory chip. If the value is returned, the memory chip is being used. If the sensor 110 is, in fact, using a memory chip, the initial read circuitry 440 may toggle the switches 402, 404 to enable the calibration signal conversion circuitry 420, as indicated by block 510. If the sensor 110 is not using a memory chip, it may be assumed that a resistor is being used and the step of enabling the calibration signal conversion circuitry 420 may not be performed. Regardless, once the switches 402, 404 are in the correct location and the calibration signal conversion circuitry 420 has been appropriately enabled or bypassed, the initial read circuitry 440 may send a message to the read circuit 310 of the monitor 130 that it can proceed collecting oximetry information from the sensor 110 via the adapter 120, as indicated by blocks 512 and 514.

Therefore, once it has been determined that the sensor 110 is using a memory chip for calibration, the calibration signal conversion circuitry 420 may convert signals received from the memory chip within the sensor 110 so that the monitor 130 can operate in the same manner as if it were connected directly to a sensor using a resistor for calibration. Again, this can be accomplished using any number of methods, a few of which will be described below. However, it should be understood that the disclosed embodiments are not intended to be limited to the particular methods disclosed below.

In an embodiment, the calibration signal conversion circuitry 420 may contain an inverse lookup table, essentially mimicking all of the lookup values listed above in Table 1 and inverting them, as shown in Table 2. To use this method, the initial read circuitry 440 may obtain the calibration curve from the memory chip in the sensor 110 and use this curve as an index to lookup the corresponding RCAL™ resistor value. Then, the initial read circuitry 440 may send an analog voltage to the read circuit 210 of the monitor 130 corresponding to the RCAL™ resistor value. To do this, the adapter 120 may be pre-programmed with an updated inverse lookup table corresponding to the lookup values used by the monitor 130. Alternatively, upon connection of the monitor 130 and the adapter 120, the calibration signal conversion circuitry 420 could interrogate the lookup table used by the monitor 130 and synchronize the values in the adapter's 120 inverse lookup table accordingly. In this manner, the inverse lookup table may function properly without pre-programming the inverse lookup table into the adapter 120 at the time the adapter 120 is manufactured.

TABLE 2

Example Inverse Lookup Values

| Calibration Curve | RCAL ™ Resistor (Ω) |
|---|---|
| Curve #1 | 1000 |
| Curve #2 | 2000 |
| Curve #3 | 3000 |
| ... | ... |
| Curve #N | N,000 |

In another embodiment, the calibration signal conversion circuitry 420 may contain an actual series of resistors that can be switched on and off to create a combined resistance through the calibration signal conversion circuitry 420 approximating the RCAL™ resistance that would have been used if the sensor 110 used a resistor for calibration purposes. This method may obviate the need for converting the signal sent to the read circuit 210 since there would be an actual resistance value in place. In other words, using this method, the calibration signal conversion circuitry 420 may physically recreate the resistance that would have been used if the sensor used a resistor for calibration purposes.

While the subject of this disclosure may be susceptible to various modifications and alternative forms, specific embodiments have been shown by way of example in the drawings and have been described in detail herein. However, it should be understood that this disclosure is not intended to be limited to the particular forms disclosed. Rather, this disclosure is to cover all modifications, equivalents, and alternatives falling within the spirit and scope of this disclosure as defined by the following appended claims.

What is claimed is:

1. An adapter, comprising:
   communications circuitry configured to facilitate communication with an oximeter sensor having a calibration element;
   communications circuitry configured to facilitate communication with an oximeter monitor;
   calibration circuitry configured to receive calibration information in a first form from the oximeter sensor and convert the calibration information into a second form which is readable by the oximeter monitor; and
   a switch configured to bypass the calibration circuitry if the calibration element of the oximeter sensor is not a digital memory chip such that the calibration information is not converted from the first form to the second form.

2. The adapter of claim 1, wherein the calibration information generally relates to wavelengths of light emitting diodes within the oximeter sensor.

3. The adapter of claim 1, wherein the first form generally relates to data values stored in the digital memory chip within the oximeter sensor.

4. The adapter of claim 1, wherein the second form generally relates to a resistance value of an expected resistor within the oximeter sensor.

5. The adapter of claim 1, wherein the calibration circuitry is configured to convert the calibration information based on values from an inverse lookup table.

6. The adapter of claim 1, wherein the calibration circuitry is configured to convert the calibration information using a series of resistors and switches.

7. The adapter of claim 1, comprising circuitry configured to convert light emitting diode signals to and from the oximeter sensor and oximeter monitor.

8. The adapter of claim 1, comprising circuitry configured to convert signals detected by a photo detector within the oximeter sensor.

9. The adapter of claim 1, wherein the adapter is configured to wirelessly communicate with the oximeter sensor.

10. The adapter of claim 1, wherein the adapter comprises an independent power source.

11. A pulse oximetry system, comprising:
an oximeter sensor having a calibration element;
an oximeter monitor; and
an adapter configured to receive calibration information in a first form from the oximeter sensor and convert the calibration information into a second form which the oximeter monitor is capable of reading, wherein the adapter is configured to switch between a first mode in which the calibration information is converted from the first form to the second form and a second mode in which conversion of the calibration information from the first form to the second form is bypassed if the calibration element of the oximeter sensor is not a digital memory chip.

12. The pulse oximetry system of claim 11, wherein the oximeter sensor comprises at least one light emitting diode, at least one photo detector, and the digital memory chip capable of storing various data regarding the oximeter sensor.

13. The pulse oximetry system of claim 11, wherein the oximeter sensor and the adapter are configured to wirelessly communicate with each other.

14. The pulse oximetry system of claim 11, wherein the adapter comprises circuitry configured to convert light emitting diode signals to and from the oximeter sensor and oximeter monitor.

15. The pulse oximetry system of claim 11, wherein the adapter comprises circuitry configured to convert signals detected by a photo detector within the oximeter sensor.

16. A method for communicating calibration information from an oximeter sensor to an oximeter monitor, comprising:
determining a type of calibration element present within the oximeter sensor;
enabling calibration signal conversion circuitry within an adapter if the calibration element is a digital memory chip;
sending a message to the oximeter monitor to begin receiving oximetry data from the oximeter sensor; and
bypassing the calibration signal conversion circuitry if the type of calibration element present within the oximeter sensor is not a digital memory chip.

17. The method of claim 16, comprising converting signals from the oximeter sensor relating to values stored in the digital memory chip into signals corresponding to expected resistance values.

18. The method of claim 16, comprising bypassing the calibration signal conversion circuitry via electrical switches.

* * * * *